United States Patent [19]

Di Ruocco et al.

[11] Patent Number: 5,362,884
[45] Date of Patent: Nov. 8, 1994

[54] MALEIMIDIC DERIVATIVES CONTAINING ACRYLIC RESIDUES

[75] Inventors: Vittorio Di Ruocco, Novara; Liliana Gila, Trino; Fabio Garbassi, Novara, all of Italy

[73] Assignee: Ministero Dell'Universita' E Della Ricerca Scientifica E Tecnologica, Rome, Italy

[21] Appl. No.: 967,125

[22] Filed: Oct. 27, 1992

[30] Foreign Application Priority Data

Oct. 29, 1991 [IT] Italy ............... MI91 A 002864

[51] Int. Cl.$^5$ ................................. C07D 207/404
[52] U.S. Cl. ....................................... 548/547
[58] Field of Search ............................ 548/547

[56] References Cited

U.S. PATENT DOCUMENTS

| | | | |
|---|---|---|---|
| 4,193,927 | 3/1980 | Baumann et al. | |
| 4,416,975 | 11/1983 | Green et al. | 430/327 |
| 5,021,487 | 5/1991 | Klemarczyk | 524/104 |
| 5,246,926 | 9/1993 | Bateson et al. | 514/202 |

FOREIGN PATENT DOCUMENTS 2030983  4/1980  United Kingdom .

OTHER PUBLICATIONS

Mar., J. *Advanced Organic Chemistry* John Wiley and Sons: New York, 1992; p. 392.
*Hackh's Chemical Dictionary*; J. Grant ed.; McGraw-Hill: New York, 1969; pp. 488, 421 and 477.
Puranik, V. G. et al. *Chem. Abstr.* 109 (22), 190899q.

*Primary Examiner*—Patricia L. Morris
*Assistant Examiner*—Michael G. Ambrose
*Attorney, Agent, or Firm*—Oblon, Spivak, McClelland, Maier & Neustadt

[57] ABSTRACT

Maleimidic derivatives containing acrylic residues having the general formula (I):

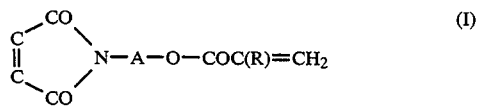

wherein R is equal to H, $CH_3$; A represents a cycloalkyl radical containing from 5 to 10 carbon atoms or an aryl radical containing from 6 to 12 carbon atoms and with the acryloxy residue —[—OCOC(R)=$CH_2$] in an ortho, meta or para position. The compounds are useful as thermostabilizing agents in structural adhesives with an acrylic base.

4 Claims, No Drawings

MALEIMIDIC DERIVATIVES CONTAINING ACRYLIC RESIDUES

The present invention relates to a group of maleimidic derivatives.

More specifically the present invention relates to a group of maleimidic derivatives containing acrylic or methacrylic residues.

These products are used as thermostabilizing agents in structural adhesives with an acrylic base.

particular the present invention relates to maleimidic derivatives having the general formula (I):

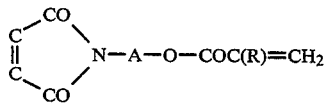

wherein R is equal to H, $CH_3$; A represents a cycloalkyl radical containing from 5 to 10 carbon atoms or an aryl radical containing from 6 to 12 carbon atoms.

Products having the general formula (I) which are preferable for the present invention are those wherein A is a cyclohexyl or a phenyl; particularly preferred are phenylmaleimide methacrylate (MPM) and phenylmaleimide acrylate.

The products having general formula (I) can be obtained with a procedure which involves reacting an acryloyl halide with an N-substituted maleimide.

The reaction is carried out in the presence of molecular sieves, in an aprotic solvent, for example dichloroethane, at a temperature ranging from 60° to 90° C.

The molecular sieves, or zeolites, are composed of hydrous aluminosilicates of alkaline or earth-alkaline metals.

Preferred molecular sieves are those of the type 3 A.

More specifically the products having general formula (I) can be obtained by means of the following reaction:

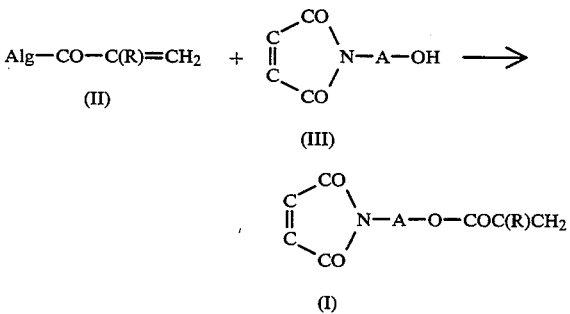

wherein R and A have the meanings specified above, and Alg is a halogen such as chlorine.

Compound (III) is well-known and can be synthesized as described in Japanese Patents 61/106,554, 79/66,671 (1979) and 79/66.670 (1979).

The following examples provide a better illustration of the present invention but do not limit it in any way.

EXAMPLE 1

12 g (0.064 moles) of N-[4-hydroxyphenyl]maleimide dissolved in 400 cc of dichloroethane are charged into a two-necked flask equipped with a mechanical stirrer, cooler, nitrogen valve and drip funnel.

16 g of molecular sieves (Union Carbide Type 3A) dried at 100° C. under vacuum for 16-18 hours, and then 30 cc (0.32 moles) of distilled methacryloylchloride are added and the mixture is heated to reflux temperature (80°-90° C.) for 26 hours, supplying fresh molecular sieves every 7-8 hours.

The solution is then washed with a solution of 2% NaOH, then with water and dried on anhydrous sodium sulphate.

The product, obtained by evaporation of the solvent, is finally washed with hexane.

7.3 g of N-[4-phenylmethacrylate]maleimide are obtained with a yield of 44.4%.

Melting point: 150°-152° C.

IR (KBr); imidic CO; 1720 $cm^{-1}$, ester CO; 1740 $c^{-1}$.
$^1$H-NMR (200 MHz, $CDCl_3$): δ 2.1(methylic H), δ 5.8-6.35 (ethylenic H); δ 6.85(maleimidic H); δ 7.2-7.4 (aromatic H).

EXAMPLE 2 (applicative)

The product synthesized in Example 1 is used as a thermostabilizing additive in an acrylic adhesive.

34.5 g of ethylmethacrylate are added to a mixture composed of: 30 g of polyethylene chlorosulphonate (commercially known as Hypalon 20), 33.8 g of methacrylic acid and 1.0 g of ethylenglycol-dimethylacrylate.

The whole quantity is mixed at room temperature, until all of the polymer has dissolved (time required: 24 hours approx.).

The adhesive paste thus obtained is completed by adding 0.3 g of di-terbutylparacresol, 0.4 g of a free radical generator of the normal type (initiator) composed of cumene hydroperoxide and 2.05 g of phenylmaleimide methacrylate (MPM).

The Brookfield of the paste is 34,000 mPa×sec.

Steel test samples 120×25×1.5 mm, treated with abrasive paper no.120, are prepared.

A layer of paste of about 0.5 mm in thickness is spread on one test sample, and on another an activator, composed of the condensation product between butyraldehyde and aniline, containing 0.1% by weight of monovalent copper, introduced as copper saccharinate.

The two adherends are coupled and compressed at a pressure of about 2 $N/m^2$.

The adhesive is post-cured at 100° C. for 1 hour after the test-samples have been joined together.

The following results are obtained:
set time: 30 seconds;
cut resistance: 20 $N/mm^2$;
cut resistance after treatment at 150° C.: 16 $N/mm^2$.

The same adhesive prepared without the addition of MPM gave a cut resistance after treatment at 150° C. of 10 $N/mm^2$.

We claim:

1. A thermostabilizing additive for an acrylic adhesive comprising a maleimidic compound of the formula (I):

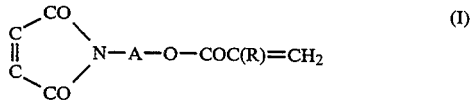

wherein R denotes H or $CH_3$; and A denotes a cycloalkyl radical containing from 5 to 10 carbon atoms or an aryl radical containing from 6 to 12 carbon atoms.

2. The thermostabilizing additive of claim 1, wherein A is selected from the group consisting of cyclohexyl and phenyl.

3. The compound phenylmaleimide methacrylate.

4. The compound phenylmaleimide acrylate.

* * * * *